United States Patent [19]
Mathiak et al.

[11] Patent Number: 5,144,844
[45] Date of Patent: Sep. 8, 1992

[54] CRUCIFORM PLANAR SPECIMEN FOR BIAXIAL MATERIALS TESTING

[75] Inventors: Friedrich Mathiak; Arnold Krawietz, both of Berlin; Horste Nowack, Siegburg; Karl-Heinz Trautmann, St. Augustin, all of Fed. Rep. of Germany

[73] Assignee: Innovationsgesellschaft fur fortgeschrittene Produktion-ssysteme in der Fahrzeugindustrie MbH, Berlin, Fed. Rep. of Germany

[21] Appl. No.: 635,627
[22] PCT Filed: Apr. 21, 1990
[86] PCT No.: PCT/DE90/00298
§ 371 Date: Mar. 4, 1991
§ 102(e) Date: Mar. 4, 1991
[87] PCT Pub. No.: WO90/13804
PCT Pub. Date: Nov. 15, 1990

[30] Foreign Application Priority Data
May 3, 1989 [DE] Fed. Rep. of Germany ....... 3914966

[51] Int. Cl.$^5$ .................................. G01N 3/00
[52] U.S. Cl. ........................................... 73/79.4
[58] Field of Search ................. 73/794, 795, 796, 797, 73/798

[56] References Cited
FOREIGN PATENT DOCUMENTS

| 3225381 | 3/1985 | Fed. Rep. of Germany . |
| 3617455 | 11/1988 | Fed. Rep. of Germany . |
| 771506 | 10/1980 | U.S.S.R. ................................. 73/795 |
| 769399 | 12/1980 | U.S.S.R. ................................. 73/794 |

OTHER PUBLICATIONS

Hardacker, K. W. Instrument and Specimen . . . of Paper, J. Phys. E: Sci. Instrum. vol. 14, No. 5, 1981, pp. 593-596.
"A Simple Testing Technique for Fracture under Biaxial Stresses", J. C. Radon et al., Experimental Mechanics, Jun. 1977, pp. 228-232.
"Influence of Load Biaxiality on the Fracture Load of Center Cracked Sheets", John Eftis et al., Int. Journ. of Fracture 20, 1982, pp. 267-288.
"Behavior of Graphite/Epoxy Plates with Holes under Biaxial Loading", Isaac Daniel, Experimental Mechanics, Jan. 1980, pp. 1-8.

*Primary Examiner*—Jerry W. Myracle
*Attorney, Agent, or Firm*—Wenderoth, Lind & Ponack

[57] ABSTRACT

A flat cross-shaped test piece is made of sheet metal for biaxially testing of its material. This test piece includes a central region that defines an area of measurement. Four arms for applying loads to the central region extend from the central region along orthogonal axes. Each arm has one end integral with the central region and an opposite end with an end part for connection to a test device for the application of a test load. Tensile stresses can thus be applied to the central region along first and second orthogonal coordinate axes of the central measurement region. Slots in the load applying arms extend along the arms parallel to the first and second coordinate axes from the end part as far as and up to the area of measurement. The slots in the load applying arms prevent the escape of stress trajectories along the arms, thus making it possible to obtain a homogenous stressed state in the central measurement region.

10 Claims, 7 Drawing Sheets

Prior Art

Prior Art

Prior Art

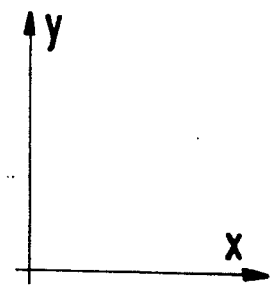
Fig.5
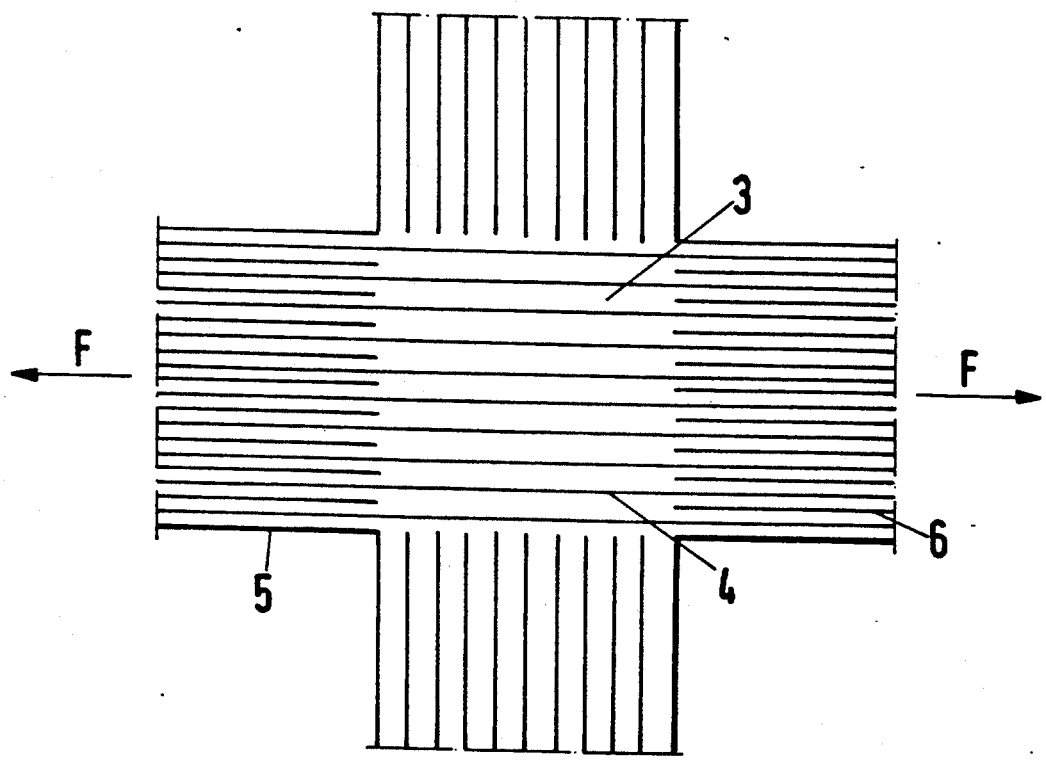

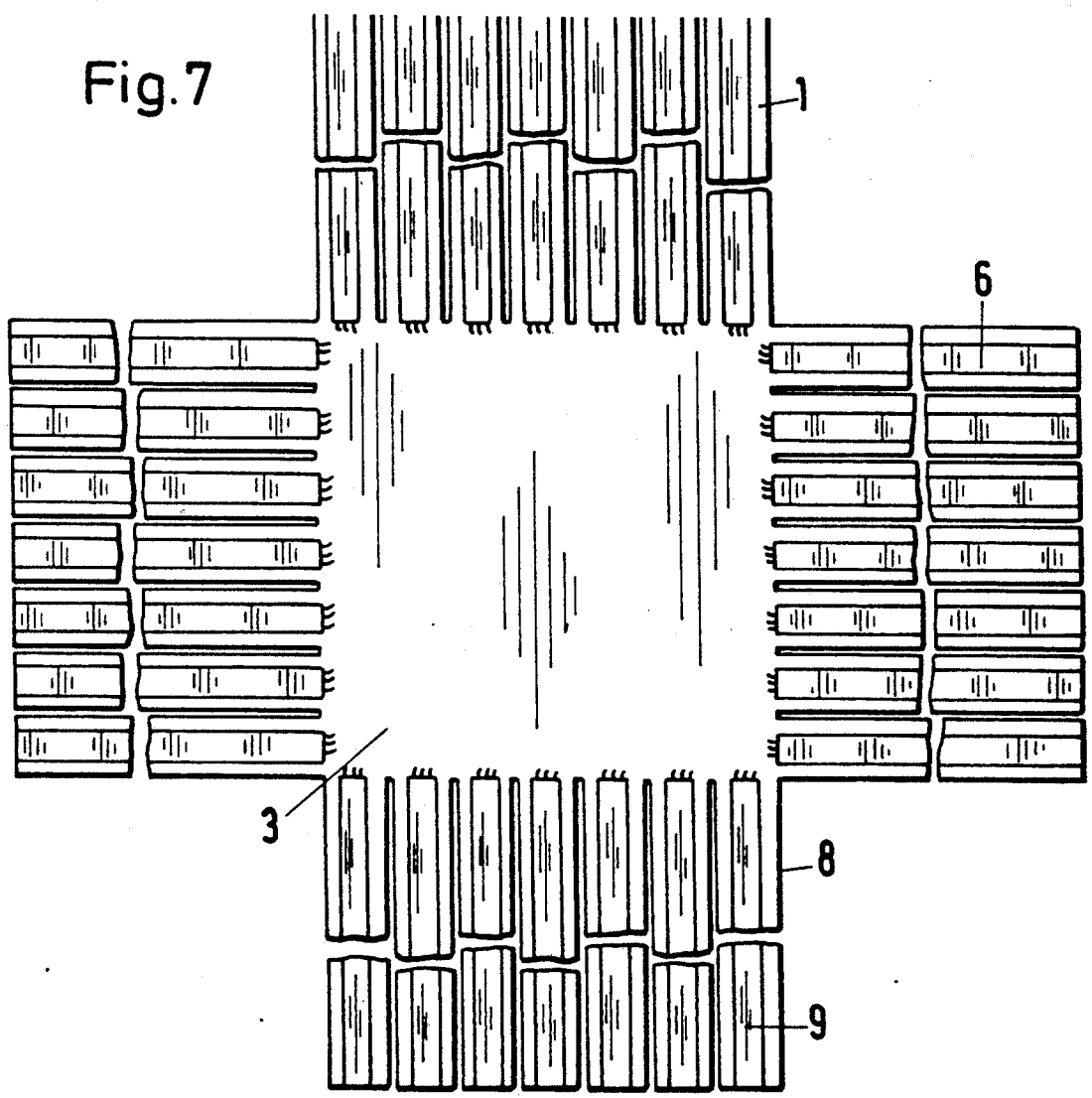
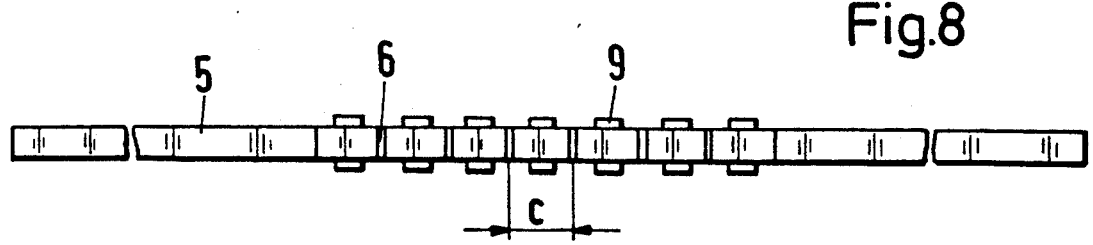
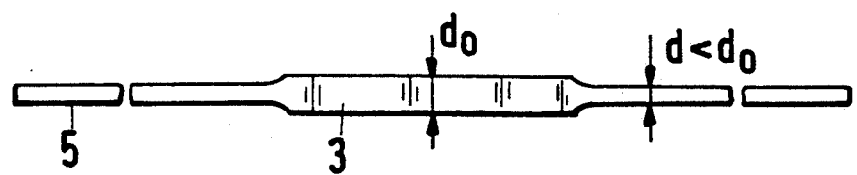

000
CRUCIFORM PLANAR SPECIMEN FOR BIAXIAL MATERIALS TESTING

BACKGROUND OF THE INVENTION

The invention relates to a cruciform, planar specimen, in particular made of sheet metal, for biaxial materials testing in a region of high strain.

To experimentally detect the nonelastic behavior of, for example, metal materials, it is necessary to determine the generally (high) biaxial strains under biaxial stresses. Homogeneous stressed and strained states in material specimens are required in order to determine the material equalizations of the so-called simple materials in the sense of Noll (W. Noll, "A New Mathematical Theory of Simple Materials," Archive for Rational Machanics and Analysis, 48.1 (1972)). Biaxial stressed states in test specimens made of sheet metal can be realized either through the use of cruciform specimens or thin-walled, tubular specimens under longitudinal force, internal pressure and torsion. An arrangement of the latter kind is, however, useful only with low strains.

Known is a planar cross specimen according to Shiratori/Ikegami (J. Mack. Phys. Solids, 1968, vol. 16, pp. 373 to 394, Pergamon Press, Great Britain) and Kreissig (dissertation Jul. 2, 1982). According to FIG. 1 of the drawings, there is illustrated a cross specimen which is suitable for the purpose of materials testing under biaxial stress in the test device according to Kreissig. Due to the static uncertainty of the known cross specimen 1 (continuum problem), the stresses cannot be determined from forces introduced in the cross specimen 1 with tensile elements 2. In a measurement region 3 provided on the specimen, the center of the cross specimen 1, no homogeneous stress and strain states can be obtained.

A cruciform planar specimen of the aforementioned kind is also known from FIGS. 5a and b of DE 32 25 381. The specimen is suitable for materials testing under biaxial stress, and is weakened in the central region by bilateral synclinal formation in order to ensure that the result of stresses will show in the region of interest in which the test forces overlap. Experiments with suitable cross specimens 1 whose central regions 3, however, are not weakened by bilateral synclinal formation, result in an escape of stress trajectories 4 under uniaxial tensile force F, as shown in FIG. 2 of the drawings. The stress trajectories 4 spread apart so that the stresses in the force direction are not constant over the width. By rerouting the stress trajectories 4, transverse stresses are produced that can lead to undesired bulges of the measurement region 3.

It is also known from DE 36 17 455, when testing materials of areal components by means of a test device for biaxial static and/or dynamic tension and/or pressure load, to provide, in assignment to the sides of the components, force transfer elements. Each force transfer element is connected to several force introducing elements generating individual loads and is arranged over the entire respective component side. With this test device, homogeneous stress and strain states cannot be attained in the areal component.

Finally, known is also a rectangular planar specimen used in a test device according to Rivlin and Saunders for rubber-like materials (Rivlin, R. S., and D. W. Saunders: Large Elastic Deformations of Isotropic Materials, VII, Experiments on the Deformation of Rubber. Phil. Trans. Roy. Soc. Lond. A 243, 251 to 288 (53, 55, 57, 67, 93, 95)). As FIG. 3 of the drawings shows, a force is introduced at the edge of the rectangular planar specimen at discrete points. This method of testing is logical only with materials that are capable of withstanding the stress peaks occurring at the load introducing elements, e.g. rubber-like materials. This method of testing is not suitable for sheet metal.

SUMMARY OF THE INVENTION

The invention addresses the problem of designing a cruciform, planar test specimen, in particular made of sheet metal, according to the aforementioned kind in such a manner that, when biaxially stressing the specimen, homogeneous stress and strain states are obtained in a measurement region in order to classify the material equalization of so-called simple materials.

The above problem is solved according to the present invention by specific embodiments and features thereof as described below According to the invention, slots designed in specimen arms forming load introducing elements make it possible to reach a homogeneous stressed state in a central measurement region of a test specimen. The stress trajectories in the central region of the specimen are prevented from escaping by the arrangement of slots in the load introducing elements.

Reinforcement of the specimen arms, according to a further feature of the invention, also makes it possible to achieve high plastic deformations in the measurement region, even with cross specimens made of deep drawn steels. Without any additional measures to reinforce the specimen arms for deep drawn steels with approximately equal tensile forces in both directions, the specimen arms would suffer high plastic strains before the measurement region would plasticize.

To reinforce the specimen arms, preferably the arms are made of a higher strength material that can be welded on to the central region. Additional materials can be used for geometrical reinforcement of the specimen arms, with the additional materials mounted on the arms. Alternatively, the specimen arms can be cold-hardened by rolling to raise the yield point.

BRIEF DESCRIPTION OF THE DRAWINGS

Embodiments of a cross test specimen according to the invention are explained below with reference to the drawing figures, wherein:

FIG. 5 is a partial top view of the cross test specimen of FIG. 4, with trajectory curves under uniaxial tensile load shown parallel to the X coordinate;

FIG. 7 is a top view of a slotted cross test specimen with geometrical reinforcement of the specimen arm according to a third embodiment of the present invention;

FIGS. 8 is a side view of the cross test specimen of FIG. 7; and

FIG. 9 is a side view of a cross test specimen with rolled specimen arms according to a fourth embodiment of the invention.

DETAILED DESCRIPTION OF THE PREFERRED EMBODIMENTS

Figure 1:
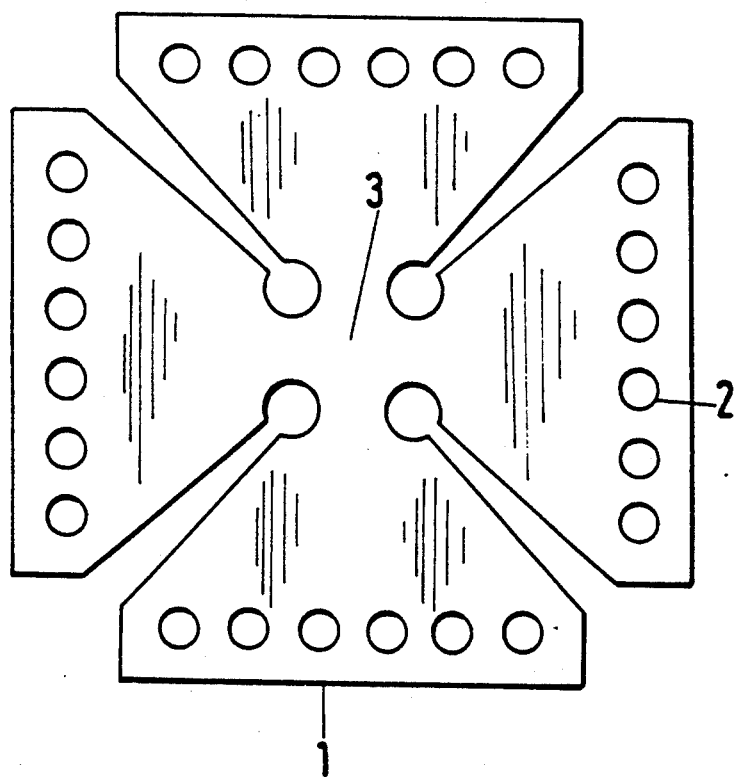
FIGS. 1–3 are respective prior art test specimens, discussed above.
Figure 2:
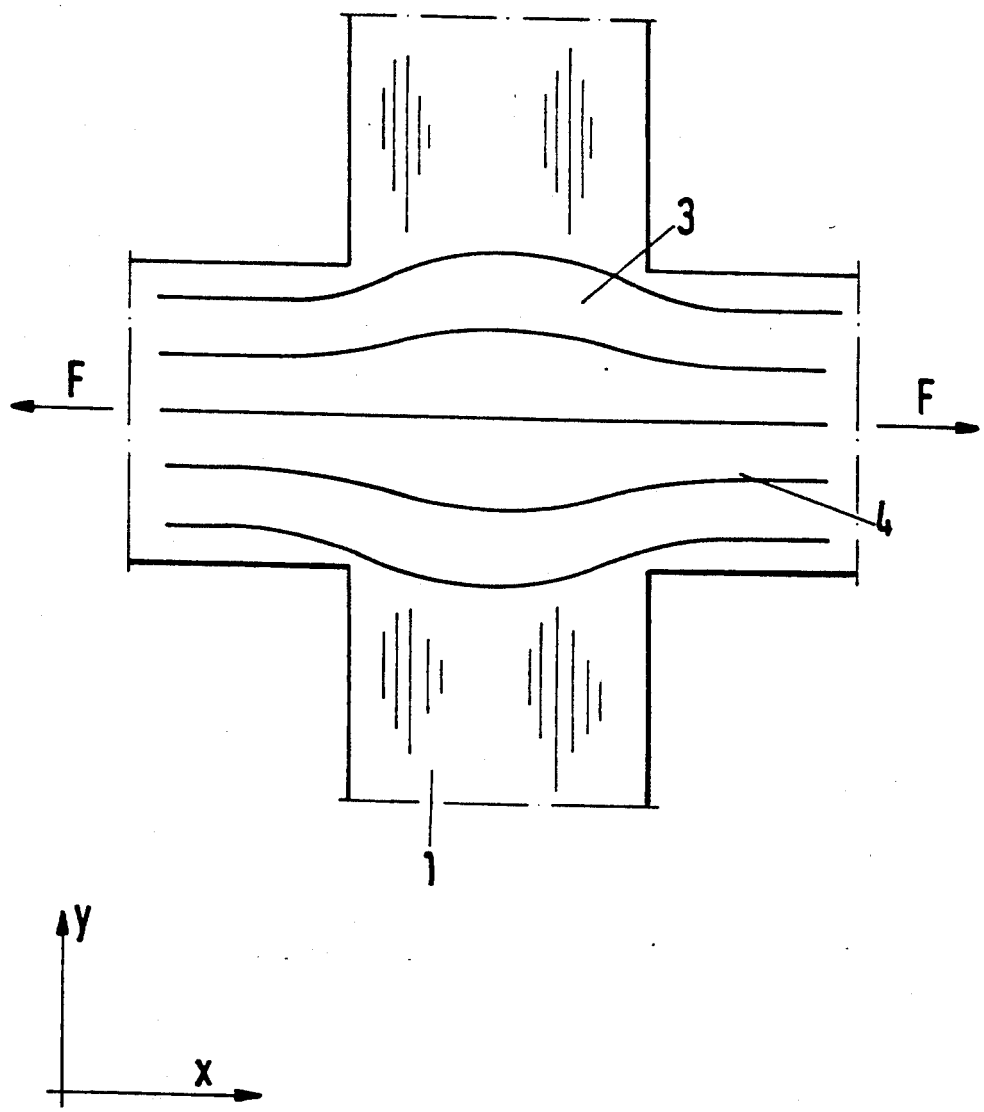
Figure 3:
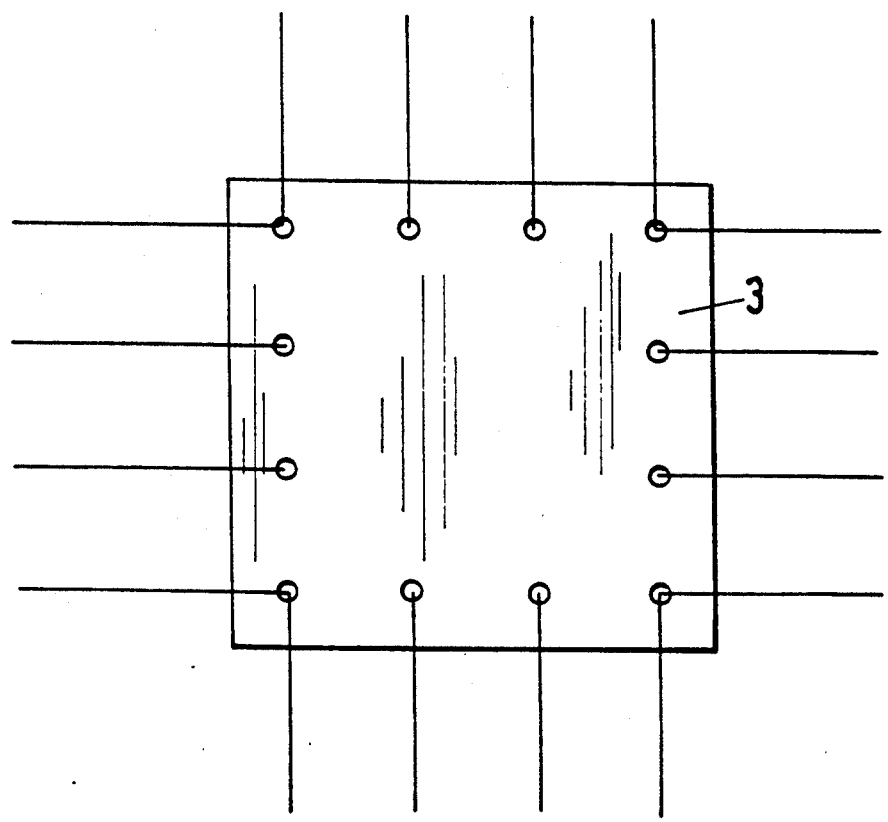
Figure 4:
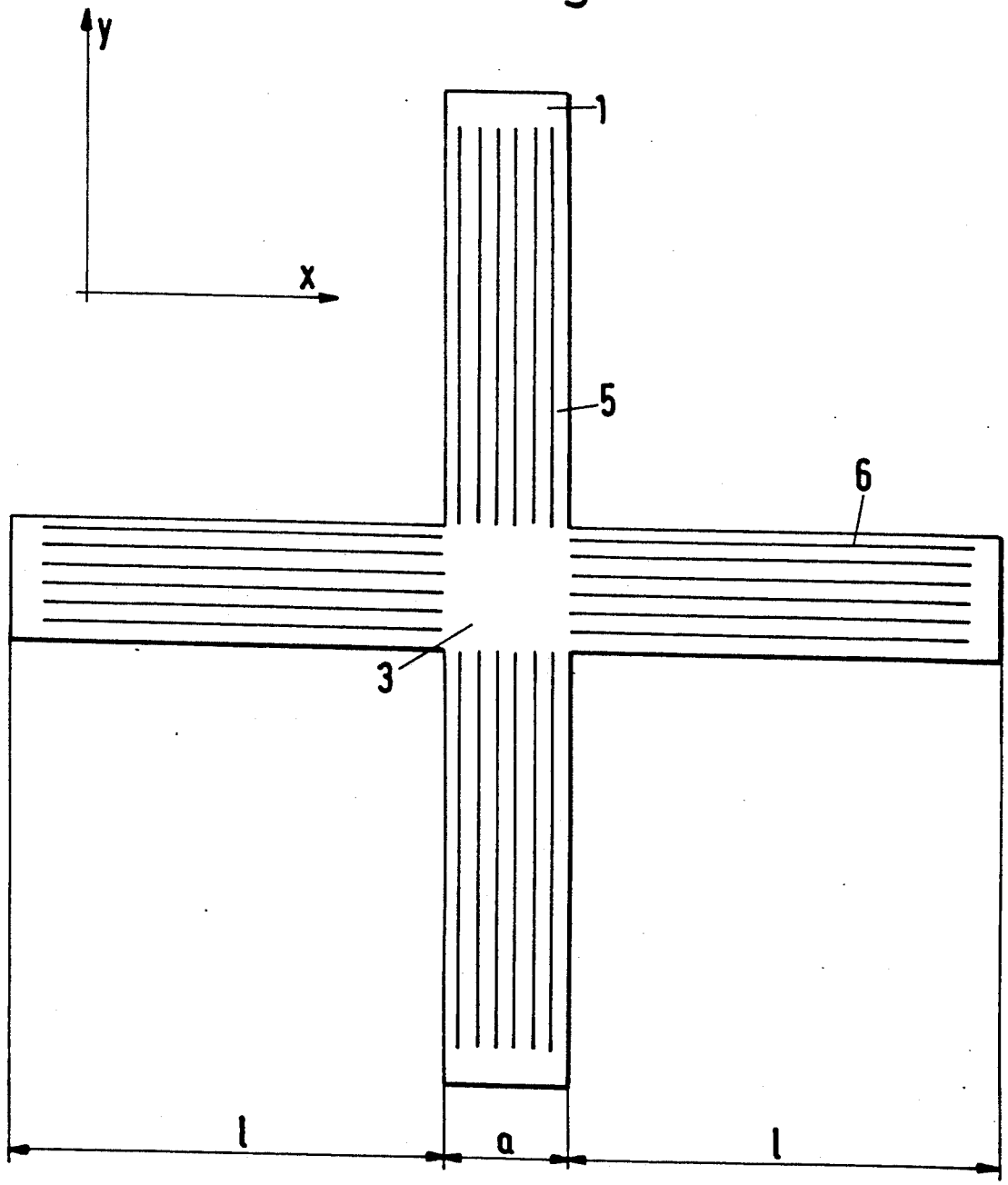
FIG. 4 is a top view of a slotted cross test specimen according to a first embodiment of the present invention.

FIG. 4 is a top view of a cross test specimen 1 having specimen arms 5 forming load applying elements with a length l and a width a. Load applying elements 5 have linear slots 6, which extend as far as and up to a central measurement region 3 of the cross test specimen 1. As FIG. 5 shows, stress trajectories 4 of the slotted cross specimen 1 under a uniaxial tensile force F extend parallel to the X coordinate in the measurement region 3 of the cross test specimen 1.

Figure 6:
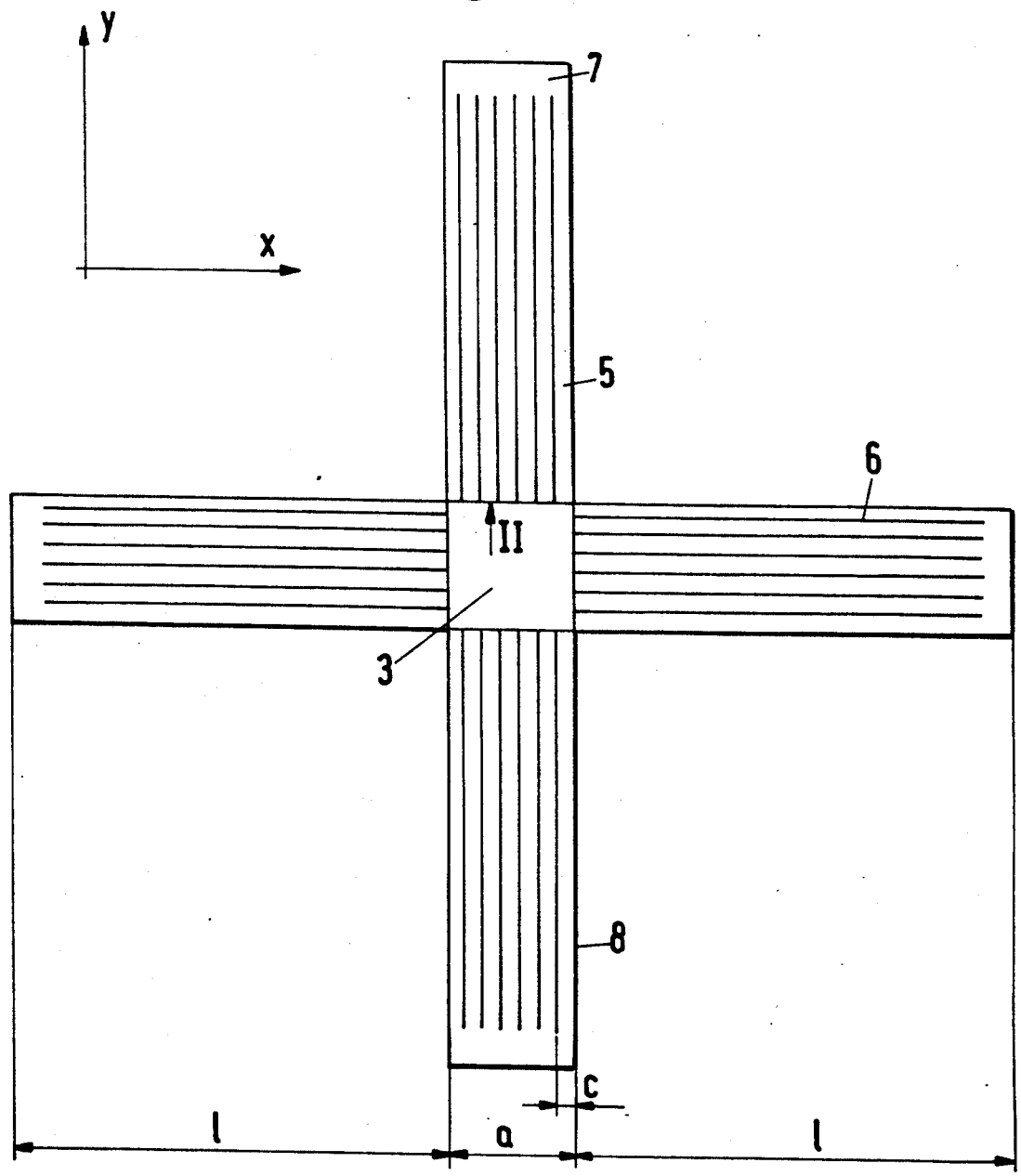
FIG. 6 is a top view of a slotted cross test specimen with welded-on arms made of a higher strength material according to a second embodiment of the present invention.

FIG. 6 is a top view of a second embodiment of the cross test specimen 1. The specimen arms 5 forming the load applying elements are welded to the measurement region 3 of the cross test specimen 1. The specimen arms 5 are made of a higher strength material than the central region 3 of the cross test specimen 1, thus effectively reinforcing the specimen arms 5, and have slots 6 extending parallel to their longitudinal direction. The slots 6 extend from an end part 7, which can be clamped in a clamping jaw of a test device. The slots 6 extend as far as the central measurement region 3 of the cross test specimen 1, and are shorter than the length of specimen arms 5 due to the end part 7. The slots 6 are uniformly spaced over the width a of each specimen arm 5, wherein the slots 6 adjacent to long edges 8 of the specimen arms also are a distance c from the long edges 8.

FIGS. 7 and 8 show another embodiment of the cross test specimen 1 in which the specimen arms 5 are reinforced by the application of additional material. The additional material is applied in the form of ribs 9 on both sides of specimen arms 5. The ribs 9 extend parallel to and between the slots 6 and between the long edges 8 of the specimen arms 5 and the neighboring slots 6. The width of the ribs 9 made of the additional material is less than distance c between the slots 6. In the central measurement region 3 of the cross test specimen 1 of FIGS. 7 and 8, homogeneous stress and strain states are also provided during biaxial material testing.

In an embodiment of the cross test specimen 1 according to FIG. 9, the specimen arms 5 are rolled, in order to raise the yield point, from thickness $d_o$ of the central region 3 of the cross test specimen 1 to a thickness d ($d<d_o$), and thus the specimen arms 5 are cold-hardened and are effectively reinforced. Even in this embodiment of the cross test specimen, homogeneous stress and strain states can be achieved under a biaxial stress in the measurement region 3.

We claim:

1. A flat cross-shaped testpiece made of sheet metal for biaxial testing of the material thereof, said test piece including:

a central regin defining an area of measurement;

four load applying arms for applying loads to said central region, each said arm having one end integral with said central region and an opposite end having an end part for connection to a test device for the application of a load, whereby tensile stresses can be applied to said central region along first and second orthogonal coordinate axes; and linear slots in said load applying arms extending along said arms parallel to said first or second coordinate axes and extending linearly from said end part as far as and up to said area of measurement;

wherein said load applying arms are reinforced in strength relative to said central region defining said area of measurement.

2. The testpiece of claim 1, wherein said slots are distributed uniformly across the width of said load applying elements.

3. The testpiece of claim 1, wherein said load applying arms are reinforced relative to said central region by making said arms of a material higher in strength than the material of said central region.

4. The testpiece of claim 3, wherein said load applying arms are welded to said central region.

5. The testpiece of claim 1, wherein said load applying arms are geometrically reinforced.

6. The testpiece of claim 5, wherein said load applying arms are geometrically reinforced by the presence of additional material on said load applying arms relative to said central region.

7. The testpiece of claim 6, wherein said additional material comprises ribs extending longitudinally on said load applying arms between said slots and between the longitudinal edges of said load applying arms and adjacent said slots.

8. The testpiece of claim 7, wherein said ribs are narrower than the distance between adjacent said slots on said load applying arms.

9. The testpiece of claim 1, wherein said load applying arms are reinforced by being hardened by cold rolling such that the yield point of said load applying arms is higher than the yield point of said central region.

10. The testpiece of claim 1, wherein said slots do not extend through said end parts of said load applying arms.

* * * * *